(12) United States Patent
George et al.

(10) Patent No.: US 8,924,229 B2
(45) Date of Patent: *Dec. 30, 2014

(54) HEALTH QUALITY MEASURES SYSTEMS AND METHODS

(75) Inventors: Jibu George, Bensalem, PA (US); Bryan Rosenberger, Pennsburg, PA (US); Charlie Jarvis, Toms River, NJ (US)

(73) Assignee: QSI Management, LLC, Irvine, CA (US)

( * ) Notice: Subject to any disclaimer, the term of this patent is extended or adjusted under 35 U.S.C. 154(b) by 155 days.

This patent is subject to a terminal disclaimer.

(21) Appl. No.: 12/721,043

(22) Filed: Mar. 10, 2010

(65) Prior Publication Data

US 2010/0235192 A1 Sep. 16, 2010

Related U.S. Application Data

(60) Provisional application No. 61/159,327, filed on Mar. 11, 2009.

(51) Int. Cl.
*G06Q 10/06* (2012.01)
(52) U.S. Cl.
CPC .................................. *G06Q 10/0639* (2013.01)
USPC ............................................................ 705/2

(58) Field of Classification Search
USPC ............................ 705/2, 3; 709/246; 707/200
See application file for complete search history.

(56) References Cited

U.S. PATENT DOCUMENTS

| | | | |
|---|---|---|---|
| 6,542,905 B1* | 4/2003 | Fogel et al. ........................... 1/1 |
| 2006/0173716 A1 | 8/2006 | Wang | |
| 2006/0282286 A1 | 12/2006 | Faris, III et al. | |
| 2007/0061393 A1 | 3/2007 | Moore | |
| 2007/0078680 A1 | 4/2007 | Wennberg | |
| 2007/0180150 A1* | 8/2007 | Eisner et al. .................. 709/246 |
| 2008/0208813 A1 | 8/2008 | Friedlander et al. | |
| 2008/0215370 A1* | 9/2008 | Dent et al. ........................ 705/3 |
| 2009/0076841 A1* | 3/2009 | Baker et al. ...................... 705/2 |

* cited by examiner

*Primary Examiner* — John Pauls
(74) *Attorney, Agent, or Firm* — Fish & Tsang, LLP

(57) ABSTRACT

Systems and methods of exchanging Healthcare Quality Measures (HQM) are disclosed. Healthcare providers can define one or more HQMs by constructing expressions using an expression builder according to a funding organization's requirements. Once a measure is derived, it can be converted to a common HQM data format and exchanged with the organization via an intermediary HQM service. The HQM data can then be converted into the organization's proprietary format. Thus, HQM data exchanges among providers and organizations are simplified.

14 Claims, 4 Drawing Sheets

HEALTH QUALITY MEASURES SYSTEMS AND METHODS

This application claims the benefit of priority to U.S. provisional application having Ser. No. 61/159,327, filed on Mar. 11, 2009. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is healthcare data flow and management.

BACKGROUND

Health organizations require healthcare providers to submit measures of the provider's performance for various reasons. One reason includes tracking provider performance measures over time to ensure quality care is provided. Another reason includes ensuring that providers meet any requirements to receive funds (e.g., grants, reimbursement, incentives, etc.). Regardless of the reasons, the known reporting systems are difficult to use and are highly inefficient.

Others have put forth effort toward coordinating communications among healthcare entities. For example, the following reference describe various aspects of healthcare quality management:

U.S. patent application publication to Wang titled "Systems and Method for Real Time Regional Feedback", filed Jan. 30, 2006, describes a system that provides for monitoring of healthcare quality measures across organization boundaries. The contemplated system allows organizations to align themselves with the industries leading performers.

U.S. patent application publication to Faris et al. titled "Evidence-Based Quality Improvement and Risk Management Solutions Method", filed Jun. 14, 2005, describes a tool selection system that selects tools to improve quality based on evidence from literature. The selection process can include determining national authoritative healthcare quality measures.

U.S. patent application publication to Moore titled "Management of Health Care Data", filed Feb. 1, 2006, provides for systems and methods of syndicating healthcare data among collaborators.

U.S. patent application publication to Wennberg titled "Systems and Methods for Analysis of Healthcare Provider Performance", filed Oct. 3, 2006, discusses using healthcare measures, both expected and actual, to determine if some services are unwarranted.

U.S. patent application publication to Friedlander et al. titled "System and Method for Quality Control in Healthcare Settings to Continuously Monitor Outcomes and Undesirable Outcomes such as Infections, Re-Operations, Excess Mortality, and Readmissions", filed Apr. 27, 2007, describes a probability analysis system that can be used within a healthcare quality measure environment.

U.S. patent application publication to Baker et al. titled "Rules-Based Software and Methods for Health Care Measurement Applications and Uses Thereof", filed Dec. 7, 2007, describes a system that coverts healthcare data into healthcare measures.

One problem with existing systems is that they fail to account for the expansive number of reporting channels among providers and/or organizations. A provider could engage with five, ten, twenty, or more organizations, while an organization could literally interface with hundreds of providers. The sheer number of engagements and communication channels is overwhelming in such a many-to-many environment. It's no wonder such communication exchanges are prone to data errors.

The issues surrounding many-to-many communication exchanges in the medical field are exacerbated by the myriad of data formats that are required for reporting healthcare quality measures (e.g., metrics). A provider is required to report measures according to five, ten or more different data formats as required by various organizations. This places an undue burden on the providers, especially smaller providers, private practices for example. Of course the reverse is true as well. An organization engages with many different providers where each provider prefers to utilize their own reporting formats.

Another problem is that each organization has proprietary requirements for establishing a measure (e.g., a metric) of performance. A provider could easily be required to submit hundreds, if not thousands of different measures across multiple organizations, where each measure has a complex set of requirements. Providers must spend considerable amounts of time to ensure they are reporting a proper measure to the correct organization.

Yet another problem associated with existing Healthcare Quality Measure (HQM) reporting solutions is that the solutions required a provider to have access to highly skilled computer labor to compile, analyze, and produce measure reports. Known systems require a provider to install and manage highly complex databases, query the databases using arcane SQL statements, and compile reports according to the various formats discussed above. The skills required for such work are often beyond the capability of a provider or beyond a provider's budget for hiring skilled labor. Unfortunately, most providers simply can not provide reports, thereby reducing their chances of obtaining funding, grants, incentives, or other benefits.

The above issues combine to create additional problems, even for those providers that do have access to the necessary skilled labor. The voluminous number of measures coupled with reporting requirements results in the provider lacking sufficient time (1) to compile relevant encounter data from their databases of patient and encounter data, (2) to analyze the compiled data to derive measures, and (3) to provide the results to the various organizations according to preferred formats. Most providers simply like time or resources to report to all desirable organizations in a timely fashion.

Thus there is a still considerable need systems, configurations, or methods for providing healthcare quality measure (HQM) reports that addresses the above issues.

SUMMARY OF THE INVENTION AND EMBODIMENTS

The present inventive subject matter is drawn to systems, configurations, and methods of providing HQM reports from healthcare providers to healthcare organizations. In a preferred embodiment, the issues surrounding the many-to-many can be alleviated through the use of an intermediary HQM service. The HQM service preferably offers capabilities to convert or translate a provider's patient and encounter data from a proprietary format to a common HQM format. Furthermore, HQM service also allows a provider to define one or more measures easily that conforms to the requirements of remote healthcare organizations. Preferred HQM services also provide reporting modules configure to submit reports having the proper measures to the various organizations. The contemplated HQM service streamlines the measure reporting process to ensure that providers can submit correct measures in reports having the correct format to the proper organizations in a timely fashion.

Healthcare providers represent entities that aid individuals with their health related needs. Providers can be an individual person, a business, an organization, or other entity. Example providers include doctors, nurses, private practices, clinics, hospitals, aid organizations (e.g., Doctors without Boarders, etc.), etc.

Healthcare organizations representing entities that monitor or fund providers. The term "organization" is used euphemistically, and should be considered to include any group (e.g., a business, organization, foundation, person, etc.). Example healthcare organizations include city, state, or federal governments, foundations, granting organizations, universities, or other organizations that likely act in a funding or sponsor capacity.

As used herein, a "measure" represents a metric of performance for a provider. In some embodiments, a measure is a ratio of a number (numerator) of patient encounters satisfying selection criteria associated with a type of care, to the number (denominator) of a base set of patient encounters. A preferred measure also comprises one or more lists of entries representing encounters, where the listed can correspond the various selecting criteria. Providing the contemplated lists, preferably through the HQM service and its associated HQM analysis modules, allow organizations to drill down into the measure data as opposed to merely receiving a number.

DETAILED DESCRIPTION

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable media. For example, a server can include one or more computers operating as a web server, database server, or other type of computer server in a manner to fulfill described roles, responsibilities, or functions. One should also appreciate that the disclosed techniques increase an efficiency of communicating healthcare data among a distributed set of healthcare entities (e.g., providers, organizations, services, etc.).

Figure 1:
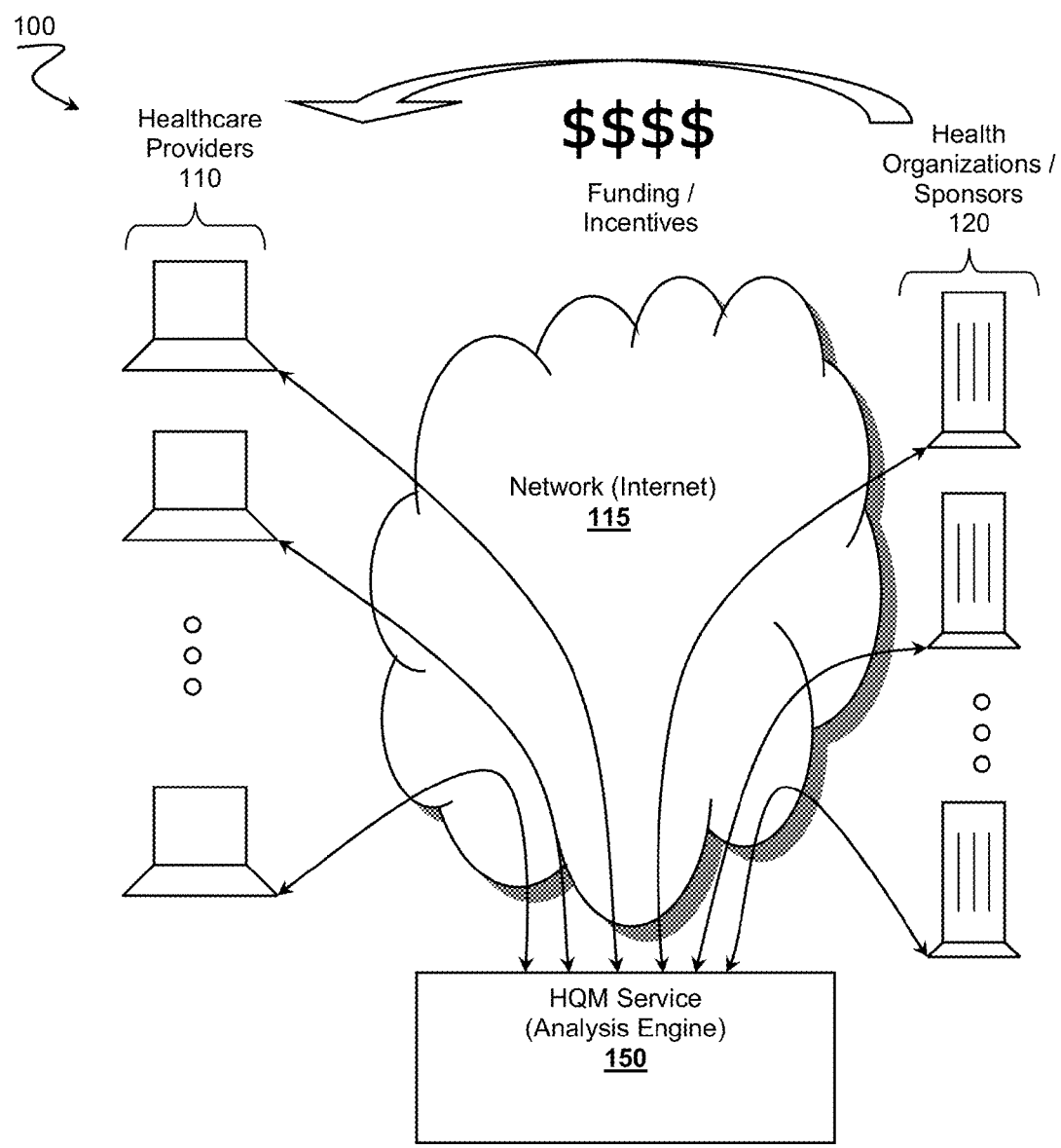
FIG. 1 is a schematic overview of a contemplated HQM system.

FIG. 1 provides a schematic overview of a contemplated HQM system 100. Multiple, unrelated healthcare providers 110 exchange HQM data 130 with multiple, unrelated health organizations 120 via an intermediary HQM service 150. The HQM service 150 provides for normalizing the various data formats, measure requirements, or reporting requirements among the participants in the HQM community. Communications, reporting, or other data exchanges preferably occur over a packet switched network 115 (e.g., the Internet, LAN, WAN, WLAN, etc.). The HQM service 150 essentially eliminates most of the many-to-many issues by flattening the communication space among the various participants. By reducing the hurdles for reporting measures to funding sponsors 120 or other organizations 120, providers 110 are able to quickly and efficiently receive funding or incentives from the organizations.

Patient or encounter data can be stored in one or more databases. Any suitable database can be used as desired. Example databases include Access, MySQL, PostgreSQL, or other commercially available database. As used herein "database" should be construed to mean a computing device configured to store and retrieve data from a storage device (e.g., HDD, SSD, CD, DVD, NAS, SAN, RAID system, etc.).

Figure 2:
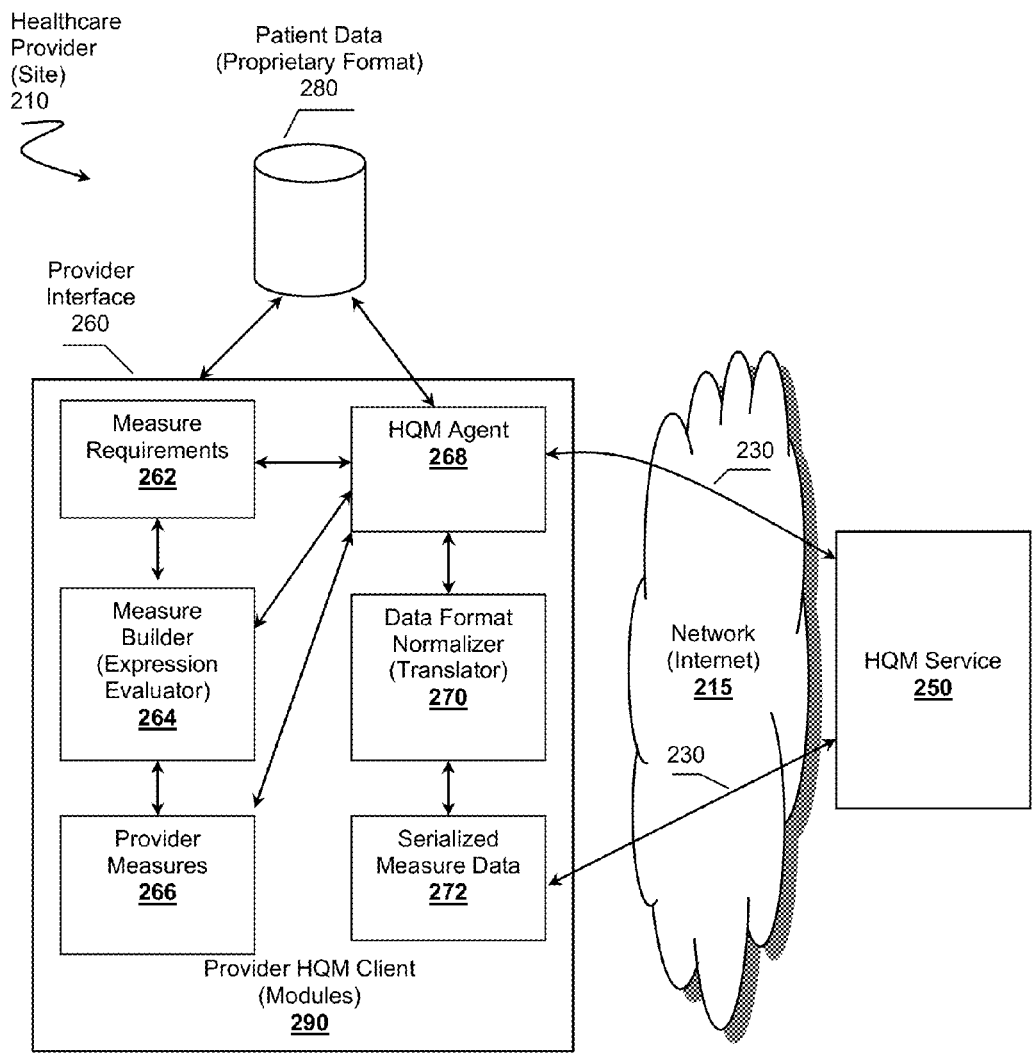
FIG. 2 is a schematic of a healthcare provider client interface to an HQM service.

Although FIG. 1 illustrates an embodiment where an HQM service 150 is accessed by the participants of the HQM community over the Internet, it is specifically contemplated that the various combinations features, capabilities, interfaces, modules, or other elements of the service FIG. 2 presents an overview of a healthcare provider site 210 where a provider utilizes a provider HQM interface 260 to access one or more capabilities of the HQM system, assuming proper authentication. As used herein the term "interface" should be consider a computing device or computing component configured to execute software instruction stored on computer readable media. The HQM interface 260 is configured to allow a provider to enter or to receive HQM related data 230 from the HQM system. Example provider HQM interfaces 260 include computers with web browsers, web services application program interfaces (API), network interfaces, or other similar interfaces that configured to present HQM information.

Preferably provider interface 260 includes the capability of receiving an organization's measure requirements 262, possibly from the HQM service 250. The service 250 can exchange measure requirements 262 among the various participants via a common HQM format to reduce risk of provider confusion. This ensures that the provider 210 can easily leverage their experience working on measures from a first organization to those of a second organization, without having to learn new measure formats or requirements. The provider 210 can use the interface 260 to access a measure builder 264 that allows provider 210 to define a measure 266 that pertains to the provider's patient data 280, regardless of the proprietary format of the data 280. Once defined, the measure 266 can be derived.

One acceptable measure builder 264 can include Next-Gen™ Expression Evaluator. A preferred measure builder 264 reduces a requirement that a provider needs highly skilled technical labor by offering the provider 210 several enhanced capabilities. For example, the measure builder 264 can utilize a data format normalizer 270 (e.g., a translator) that can automatically convert encounter data 280 from a provider's data format to the common HQM format. Another capability allows the provider to drag-and-drop, or to point-and-click in order to modify elements of a measure expression to build a measure 266, without requiring the provider 210 to draft complex SQL queries. The expression elements can include parameters, constants, lists of encounter entries to be processed or analyzed, operators, or other expression elements.

In some embodiments, the HQM service 250 communicates with a HQM agent 268 that is configured to exchange data 230 with the remote HQM service 250 and with the provider 210 via the provider interface 260. The agent 268 can receive provider defined measures 266 and possibly derive the actual measure 266 from the patient data 280. Once the measure information is collected from the patient data 280, the agent can normalize the data into a common HQM data format (e.g., serialized measure data 272) via the data format normalizer 270. The measure information can be serialized, possibly using XML or other serializing format, and sent back as data 230 over a network 215 to the HQM service 250.

One should appreciate that the provider HQM interface 260 can be embodied by a computer system having one or more HQM client software modules 290 installed. Alternatively, the computer system could include a web browser that accesses the provider interface capabilities from an HTTP server, either locally resident at the provider site 210 or remote from the provider site 210.

Figure 3:
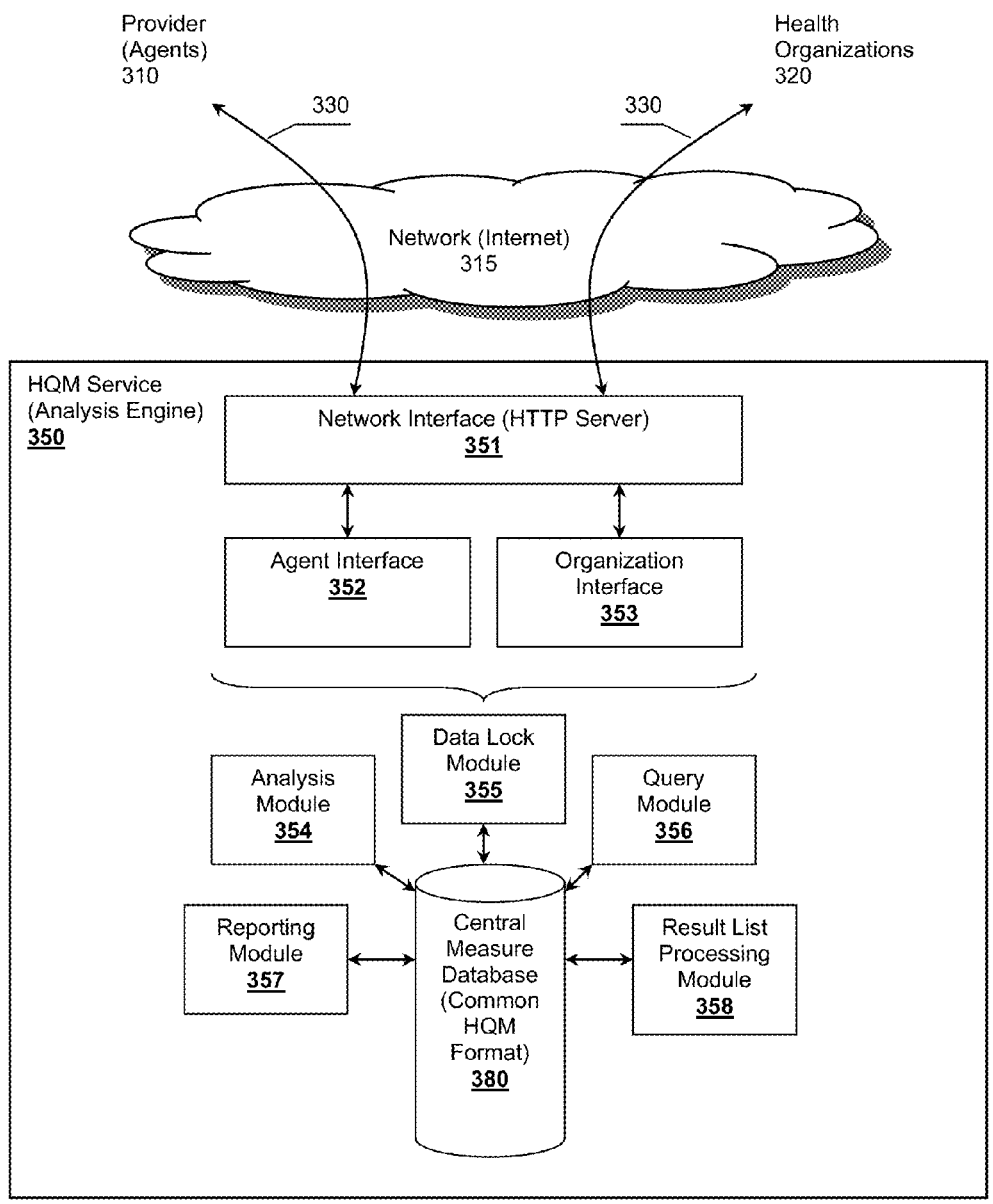
FIG. 3 is a schematic of an HQM service capable of operating as an analysis engine.

FIG. 3 illustrates a possible embodiment of an HQM service 350 implemented as a web service accessible over a network 315. In a preferred embodiment, an HQM service 350 comprises an HQM analysis engine 350 capable of processing various measures from providers 310 as required by various organizations 320. The HQM analysis engine 350 can include a network interface 351, possibly an HTTP server, configured to communicate to remote participants in the HQM community including providers 310 or organizations 320. For example, the analysis engine 350 can utilize an agent interface 352 through which it can exchange data 330 with provider HQM agents (e.g., commands, serialized HQM data, queries, etc.), or other aspect of a provider HQM client. Additionally, the engine 350 can employ an organization interface 353 through which the engine 350 can exchange measure requirements, reports, or other HQM related information with remote organization HQM clients 320.

As used herein, the term "engine" should be considered a computing device configured to execute software instructions stored on a computer readable medium. Preferably the software instructions include HQM analysis capabilities for deriving measures from normalized encounter data obtained from provider's patient databases.

A preferred HQM analysis engine 350 comprises one or more modules capable of interacting with the agent interface or organization interface. Example modules include an analysis module 354 configured to access encounter data stored in a central or remote database 380, and configured to derive one or more measures. Another module can include a reporting module 357 capable of generating a measure report from a derived measure where the report conforms to the reporting requirements of an organization 320. Yet another module can include a data lock module 355 that allows the HQM service 350 to restrict access to data (e.g., encounter or non-encounter data) at a remote site to ensure the data is stable before being downloaded, or uploaded. Still another possible module includes a list processing module 358 used to process result sets as part of a measure, or generated while deriving a measure. Still yet another module can include query module 356 that allows remote participants to submit HQM queries to the engine 350, which can then generate lists (e.g., a result set) that satisfy the query.

In a preferred embodiment, an HQM analysis module 354 derives a measure by applying one or more measure selection criterion to encounter data, possibly stored locally or via an HQM agent at a provider site 310. Preferably the selection criteria is used generate one or more lists, each list having entries corresponding to encounters that satisfied the selection criteria. The lists can then be used to derive a measure.

As discussed previously, a provider 310, or other member of the community, can define a measure by creating an expression that can be evaluated. The expression comprises one or more elements of parameters, operators, or other selection criteria that used to select data entries from the various databases. The results of applying the expression is preferably a list of database entries from one or more databases representing encounters that satisfy the expression. The lists can then be used for further analysis to derive the measure. The measure can be a simple, single value metric (e.g., ratio of a numerator to denominator), or a multi-valued data set comprising a metric and all the lists, or list entries, that went into a forming the measure. In a preferred embodiment, the measure data is stored in the common HQM format.

Once the various lists are generated, they can be processed via the list processing module 358. The list processing module can create new lists, merges lists, prune lists, filter lists, or otherwise support analysis of the data via list processing. It should be appreciated that lists are result sets of filters placed on encounter data, where each entry in the encounter data can be considered an n-tuple. Such an approach provides for quick, efficient analysis of provider performance measures, either automated via the HQM service 350, or even manually by the provider 310 or organization 320.

Figure 4:
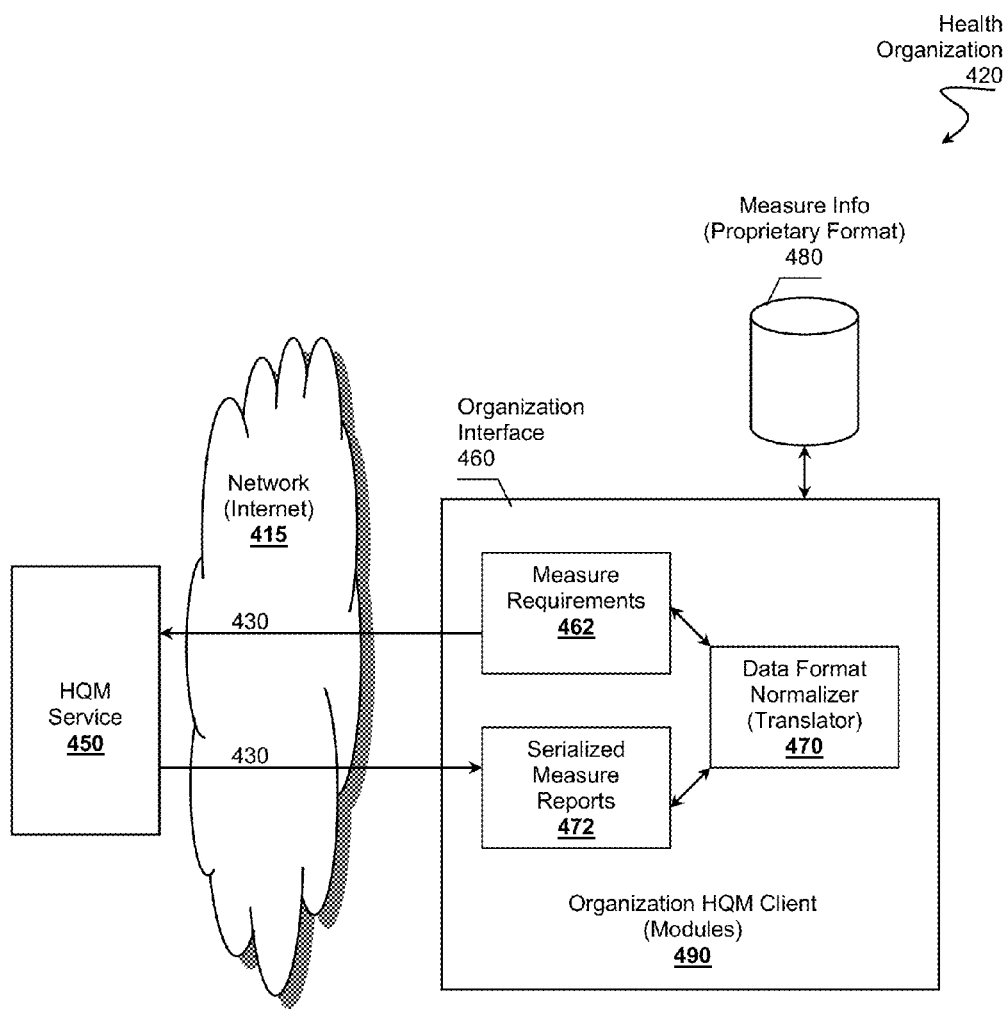
FIG. 4 is a schematic of a healthcare organization client interface to an HQM service.

FIG. 4 illustrates a schematic of an embodiment where a health organization site 420 interfaces with the HQM service 450, assuming proper authentication, via an organization interface 460 represented by an organization HQM client 490. Healthcare data 430 can be exchanged over network 415. In a preferred embodiment the organization interface 460 is configured to send measure requirements 462 or other HQM reporting information to the HQM service 450. Additionally, the organization interface 460 is preferably configured to receive HQM reports 472, possibly in a serialized format. It is also contemplated, that the organization interface 460 can include a data format normalizer 470 (e.g., a translator) that can convert from a common HQM data format to a proprietary format used by the organization to store measure information 480.

One should appreciate that the various elements or functionality of the disclosed system can be moved from one location (e.g., provider, HQM engine, organization, etc.) to another without departing from the main concepts of the inventive subject matter. All arrangements of functionality are contemplated. Furthermore, one should also appreciate that the disclosed elements can be embodied by hardware or software installable at the various sites (e.g., the provider site, HQM service site, organization site, etc.)

Thus, specific compositions and methods of the inventive subject matter have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A method of reporting a health quality measure (HQM), the method comprising:

providing, for a plurality of healthcare providers, access to an HQM service, comprising at least one computer, that is coupled to a first funding organization and a second funding organization, the HQM service configured to receive, from each of the plurality of healthcare providers, patient data in a proprietary format corresponding to the healthcare provider and convert the received patient data from the proprietary format to a common HQM data format;

providing a healthcare provider interface coupled to the HQM service computer;

allowing each of the plurality of healthcare providers to use the healthcare provider interface to define a first mathematical expression that uses at least some of the patient data corresponding to the healthcare provider for computing a first HQM according to requirements of the first funding organization;

deriving, by the HQM service, the first HQM for each of the plurality of healthcare providers based on the patient data corresponding to the healthcare provider and the first mathematical expression defined by the healthcare provider;

upon request by the first funding organization, generating, by the HQM service computer, a first HQM report having the derived first HQM, where the report is automatically formatted according to requirements of the first funding organization; and automatically sending, by the HQM service computer, the generated first HQM report to the first funding organization.

2. The method of claim 1, wherein the step of allowing each of the plurality of providers to define the first mathematical expression for computing the first HQM includes authenticating the provider with respect to the HQM service.

3. The method of claim 1, wherein the step of deriving the first HQM is conducted by an HQM agent that is a client-side software application configured to operate on a second computer at the provider's site.

4. The method of claim 1, wherein the first mathematical expression for computing the first HQM comprises a numerator and a denominator, wherein the step of deriving the first HQM includes calculating a numerator representing a number of encounters in the patient data that satisfy the selection criteria of the numerator portion, and calculating a denominator representing a number of encounters in the patient data that satisfy the selection criteria of the denominator portion.

5. The method of claim 4, further comprising calculating the first HQM as a ratio of the numerator to the denominator.

6. The method of claim 1, further comprising using the HQM service computer to generate a plurality of lists containing encounter data entries obtained from the patient data where each of the entries represents an encounter that satisfies individual selection criterion of the selection criteria from at least one of the numerator portion and the denominator portion.

7. The method of claim 6, wherein the first HQM comprises at least some of the plurality of lists.

8. The method of claim 1, wherein the step of allowing the provider to define the first mathematical expression for computing the first HQM includes allowing the provider to drag and drop elements of selection criteria within the provider interface to form the first HQM.

9. The method of claim 1, further comprising:

allowing each of the plurality of healthcare providers to use the healthcare provider interface to define a second mathematical expression that uses at least some of the patient data corresponding to the healthcare provider for computing a second HQM according to requirements of the second funding organization;

deriving, by the HQM service, the second HQM for each of the plurality of healthcare providers based on the patient data corresponding to the healthcare provider and the second mathematical expression defined by the healthcare provider;

upon request by the second funding organization, generating, by the HQM service computer, a second HQM report having the derived second HQM, wherein the report is automatically formatted according to requirements of the second funding organization; and automatically sending an the generated second HQM report having the second HQM to a second funding organization.

10. A healthcare quality measure (HQM) analysis engine comprising a computer, the engine further comprising:

an HQM database storing HQM data in a common HQM data format where the HQM data represents patient data obtained from a plurality of healthcare providers, the patient data from each of the plurality of healthcare providers is in a proprietary data format corresponding to the healthcare provider;

a network interface communicatively coupled to the plurality of healthcare providers via a packet switched network and configured to allow each of the plurality of healthcare providers to define a mathematical expression that uses at least some of the HQM data corresponding to the healthcare provider for computing an HQM according to requirements of a first funding organization and store the encounter data mathematical expression in the HQM database;

an HQM analysis module configured to derive a measure for each of the plurality of healthcare providers based on the HQM data corresponding to the healthcare provider and the mathematical expression defined by the healthcare provider;

a HQM reporting module configured to generate, for the first funding organization, an HQM report based on the derived measures of the healthcare providers, where the generated report is automatically formatted according to requirements of the first funding organization; and an organization interface communicatively coupled to the plurality of healthcare organizations via a network and configured to present the generated HQM reports to the first funding organization via the network.

11. The engine of claim 10, wherein the HQM analysis module is further configured to generate one or more lists containing entries representing patient data from the HQM data corresponding to HQM selection criteria, wherein the lists are stored within the HQM database.

12. The engine of claim 10, further comprising a list processing module configured to merge two or more lists into a single list according to one or more selection criterion of the HQM selection criteria.

13. The engine of claim 10, wherein the HQM database stores one or more measure requirements from the first funding organization.

14. The engine of claim 10, further comprising an HQM data lock module configured to restrict access to a remote healthcare provider's patient data.

* * * * *